United States Patent
Nelson

(10) Patent No.: US 6,266,997 B1
(45) Date of Patent: Jul. 31, 2001

(54) THERMAL MANAGEMENT OF A SENSOR

(75) Inventor: Charles Scott Nelson, Clio, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/276,623

(22) Filed: Mar. 25, 1999

(51) Int. Cl.[7] .......................... G01N 27/26; G01N 27/04; G01N 31/12

(52) U.S. Cl. .................. 73/31.05; 73/31.05; 73/23.31; 73/23.32; 204/426; 338/34; 338/230; 422/94

(58) Field of Search ................... 73/31.05, 23.31, 73/23.32, 23.2, 118.1; 422/94, 109; 204/426, 424; 338/34, 229, 274, 275

(56) References Cited

U.S. PATENT DOCUMENTS

| | | | | |
|---|---|---|---|---|
| 4,237,722 | * | 12/1980 | Achari | 73/23 |
| 4,308,518 | * | 12/1981 | Hattori et al. | 338/34 |
| 4,911,892 | * | 3/1990 | Grace et al. | 422/94 |
| 5,602,325 | * | 2/1997 | McClanahan et al. | 73/23.31 |
| 5,616,825 | * | 4/1997 | Achey | 73/23.31 |
| 5,739,414 | * | 4/1998 | Paulus et al. | 73/23.31 |
| 5,817,920 | * | 10/1998 | Kuisell et al. | 73/23.31 |
| 5,886,248 | * | 3/1999 | Paulus et al. | 73/23.31 |
| 6,082,175 | * | 7/2000 | Yoshikawa et al. | 73/23.31 |
| 6,101,865 | * | 8/2000 | Meixner et al. | 73/23.32 |

* cited by examiner

Primary Examiner—Hezron Williams
Assistant Examiner—David J. Wiggins
(74) Attorney, Agent, or Firm—Vincent A. Cichosz

(57) ABSTRACT

In an exemplary embodiment, the present invention provides an exhaust constituent sensor comprising a planar sensing element securely held in place within a tubular inner shield by known methods. Improved thermal management of the sensor is provided by disposing a thermally conductive material between said planar sensing element and said tubular shield. In an exemplary embodiment, the thermally conductive material comprises a high thermal conductivity metal mesh which transfers heat within said tubular shield to said tubular shield via thermal conduction. The heat is then dissipated into the surrounding environment via thermal convection at an outer surface of the tubular shield. By optionally disposing an annular heat fin on the outer surface of the tubular shield, a greater amount of heat is dissipated into the surrounding environment via thermal convection in less time.

26 Claims, 4 Drawing Sheets

THERMAL MANAGEMENT OF A SENSOR

TECHNICAL FIELD

The present invention relates generally to planar sensors. More particularly, the present invention relates to a planar sensor having improved thermal management, especially in a high temperature environment, as for example in an exhaust constituent sensor.

BACKGROUND OF THE INVENTION

Exhaust constituent sensors have been used for many years in automotive vehicles to sense the presence of constituents in exhaust gasses (e.g., oxygen, hydrocarbons, nitrous oxides) and to sense, for example, when an exhaust gas content switches from rich to lean or lean to rich. One known type of exhaust constituent sensor includes a flat plate sensor formed of various layers of ceramic and electrolyte materials laminated and sintered together with electrical circuit and sensor traces placed between the layers in a known manner.

Because automotive exhaust constituent sensors are mounted to members of the vehicle exhaust flow system, the sensors must be durable and the sensors must be able to operate in a high temperature environment without being damaged by exposure to such high temperatures. The exhaust constituent sensors are typically installed in an exhaust pipe which is part of the motor vehicle's exhaust flow system and more specifically, the exhaust constituent responsive end of the sensor is disposed within an opening in the exhaust pipe so that exhaust gasses flow into the sensor and the level of the exhaust constituent to be sensed is communicated to a control system of the motor vehicle.

Typically, most exhaust constituent sensors have approximately the same length due to temperature requirements of a seal material and a terminal connection at one end of the sensor. More specifically, the length of the portion of the sensor which extends away from the exterior of the exhaust pipe is approximately the same for all conventional sensors to prevent excessive heat from traveling upward within the sensor to the seal material and the terminal connection. Consequently if the length of the sensor is too short, excessive heat is more likely to travel upward and contact the seal material and the terminal connection. Thus by extending the length of the sensor, the temperature of the heat is sufficiently reduced over time as it travels the length of the sensor and the seal material and the terminal connection are thermally protected and disposed away from the exhaust pipe, which reaches high temperatures during use of the motor vehicle. This is especially true for exhaust constituent sensors which are mounted in a spark ignition gasoline engine, close to the manifold outlet. The reasons for this is that most planar sensors are built with several air "pockets" preventing heat that is in the middle of the sensor from escaping out to the cooler outside diameter.

SUMMARY OF THE INVENTION

The present invention comprises exhaust constituent sensors and a method of manufacturing same, and more particularly relates to an exhaust constituent sensor having improved thermal management in a robust simple package. An exemplary embodiment comprises an exhaust constituent sensor, comprising a planar sensing element securely held in place within a tubular inner shield by methods known in the art. In accordance with the present invention, a thermally conductive material is disposed between the tubular shield and the planar sensing element, wherein the thermally conductive material preferably comprises a high thermal conductivity metal mesh. The thermally conductive material is disposed at a predetermined location within the sensor so that any heat which travels within the tubular shield toward the electrical connection at one end of the sensor is effectively transferred to an inner surface of the tubular shield by the thermally conductive material. The heat is then further dissipated via thermal convection which occurs at an outer surface of the tubular shield and the heat is effectively transferred into the surrounding environment.

In order to increase the rate and amount of heat which is transferred into the surrounding environment via thermal convection, an annular heat fin may be optionally provided on the outer surface of the tubular shield. The annular heat fin is designed to facilitate heat transfer via convection by providing an outer surface which thereby increases the general surface area available for thermal convection to occur so that excessive heat is transported and dissipated prior to being permitted to travel upward in the tubular shield toward the electrical connection.

BRIEF DESCRITION OF THE DRAWINGS

The present invention will now be described by way of example with reference to the following Figures, which are meant to be exemplary, not limiting, and in which.

DETAILED DESCRIPTION OF THE INVENTION

Figure 1:
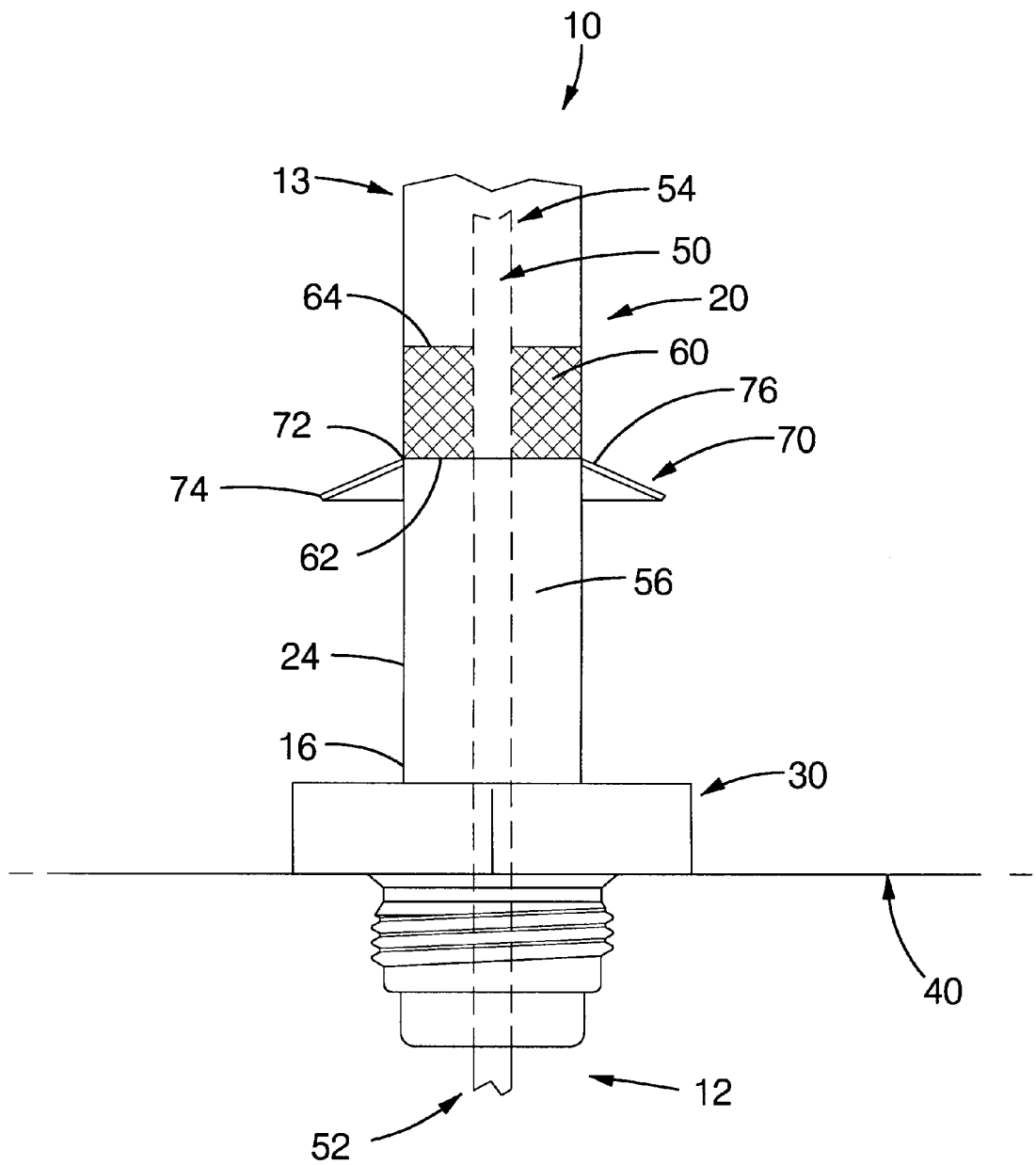
FIG. 1 is a simplified cross-sectional side view of a portion of an exhaust constituent sensor embodying the present invention.

FIG. 1 is a simplified cross-sectional view of a portion of an exemplary exhaust constituent sensor of the present invention, generally designated as 10. Exhaust constituent sensor 10 includes a housing structure generally formed in part of a tubular shield 20 and a shell 30 which holds tubular shield 20. Shell 30 acts as a sensor mount permitting the easy installation of sensor 10 within a member which carries the fluid to be sensed, preferably a gas constituent in exhaust gas, whereby sensor 10 is mounted within the fluid carrying member. Typically, the fluid carrying member comprises an exhaust pipe 40 of a motor vehicle, wherein exhaust constituent sensor 10 is installed within an opening (not shown) in exhaust pipe 40 so that one end 12 of exhaust constituent sensor 10 is disposed within the normal flow of exhaust gas through exhaust pipe 40. Shell 30 is preferably designed to both provide a gas tight seal between exhaust pipe 40 and exhaust constituent sensor 10 when sensor 10 is inserted into the opening of exhaust pipe 40 and to securely position exhaust constituent sensor 10 within exhaust pipe 40 so that exhaust constituent sensor 10 receives sufficient fluid when disposed within exhaust pipe 40.

Preferably, a planar sensing element 50 is held by known methods inside tubular shield 20. Planar sensing element 50 is an exhaust sensing element of a known type with any conventional geometry, such as a generally flat elongated rectangular shape. At a first end 52 thereof, planar sensing element 50 includes a gas-responsive structure fabricated into planar sensing element 50 in a known manner, preferably along with a heater (not shown) of a known type. At an opposite end 54 of planar sensing element 50, the lower end of at least one electrical terminal (not shown in FIG. 1) contacts external pads (not shown) on end 54 to provide electrical connection between the at least one terminal and planar sensing element 50.

The present invention provides a transport mechanism to transfer excessive heat from an inner cavity 56 to an outside diameter of exhaust constituent sensor 10 to prevent excessive heat from traveling upward in sensor 10 from exhaust pipe 40 and contacting a cable seal material and a terminal connection (not shown). The heat is then removed or dissipated via thermal convection in which the heat is diffused into the environment surrounding the outside diameter of exhaust constituent sensor 10. As is known in the art, convection involves the diffusion of energy (heat) in which the fluid as a whole is moving in the direction of the diffusion. More specifically, as the level of heat increases in a central portion 16 of exhaust constituent sensor 10, the heat is transferred via conduction from inner cavity 56 to an inner surface of tubular shield 20 by disposing a thermally conductive material 60 between planar sensing element 50 and tubular shield 20. As is illustrated in FIG. 1, thermally conductive material 60 preferably comprises a metal mesh material concentrically disposed around planar sensing element 50. Thermally conductive material 60 includes a first end 62 and a second end 64, wherein first end 62 is located closer to shell 30 and central portion 16 of exhaust constituent sensor 10. First end 62 of thermally conductive material 60 will generally be exposed to higher temperatures during operation of exhaust constituent sensor 10 due to it being in closer proximity to exhaust pipe 40, while second end 64 extends away from exhaust pipe 40 and is located in closer proximity to the electrical terminals (not shown in FIG. 1).

Although thermally conductive material 60 can be disposed anywhere along tubular shield 20, it is preferably disposed at an end 13 of tubular shield 20 adjacent the terminal connection (not shown) of sensor 10 in order to optimize its thermal transfer capacity and efficiency. At end 13, opposite end 12 which is proximate exhaust pipe 40, temperatures outside tubular shield 20 are cooler than outside temperatures at end 12 due to heat emitted by exhaust pipe 40. Consequently, to optimize the efficiency of the thermal transport mechanism of the present invention, thermally conductive material 60 should be disposed where the temperatures outside sensor 10 are cooler. Thus, to optimize thermal transfer capacity and efficiency, thermally conductive material 60 is disposed adjacent the terminal connection of sensor 10 at end 13 opposite end 12 and exhaust pipe 40. As is clear from FIG. 2, thermally conductive material 60 is preferably disposed adjacent the terminal connection of the sensor to transfer and dissipate excessive heat prior to the heat contacting the terminal connection at elevated temperatures over a continuous period of time. For example, the terminal connection is preferably not continuously exposed to temperatures exceeding about 340° C.

By disposing thermally conductive material 60 concentrically around planar sensing element 50 and preferably in intimate contact with planar sensing element 50 and tubular shield 20 of exhaust constituent sensor 10, heat contained within inner cavity 56 is effectively transferred to the outside diameter of exhaust constituent sensor 10 via conduction. As is known in the art, conduction involves the transmission of energy by a medium which does not involve movement of the medium itself. Thus, thermally conductive material 60 transfers heat from inner cavity 56 to the inner surface of tubular shield 20, whereby the heat is further dissipated and transmitted via convection and the heat dissipates from an outer surface 24 of tubular shield 20 into the immediately surrounding environment. Thermally conductive material 60 also functions to provide support for planar sensing element 50 and securely hold the same in place within tubular shield 20.

Thermally conductive material 60 comprises suitable thermally conductive materials and in an exemplary embodiment, thermally conductive material 60 comprises a high thermal conductivity metal designed for use in a high temperature environment, such as a spark ignition engine environment where temperatures range between about 300° C. and about 1000° C. High thermal conductivity metal is commercially available from a number of sources and one preferred high thermal conductivity metal comprises a stainless steel metal mesh and more preferably a stainless steel metal mesh having an SAE (Society of Automotive Engineers) designation of SS (stainless steel) 400 series. The higher the density of the metal mesh (i.e. percent of solid) that is used, the better the thermal conductivity. However, mesh densities above about 50% tend to be difficult to install within the interior of exhaust constituent sensor 10 despite being equally suitable in terms of conductance for use in exhaust constituent sensor 10. Accordingly, a preferred high thermal conductivity metal comprises metal meshes having a mesh density of about 55% or less.

Thermally conductive material 60 and more specifically, high thermal conductivity metal mesh, may be disposed within exhaust constituent sensor 10 by methods known in the art. A preferred method of disposing the high thermal conductivity metal mesh within exhaust constituent sensor 10 employs a metal mesh having a mesh density of about 50% and disposes the same within exhaust constituent sensor 10 in a "slip fit" manner. A "slip fit" manner refers to the situation where the diameter of thermally conductive material 60 (metal mesh) is less than the inner diameter of tubular shield 20. As a result, thermally conductive material 60 is easily installed or disposed within tubular shield 20 and some movement of thermally conductive material 60 is permitted within tubular shield 20. Thermally conductive material 60 is then preferably crimped in place to secure the metal mesh in place and to provide a good conductive path to the inner surface of tubular shield 20.

Figure 2:
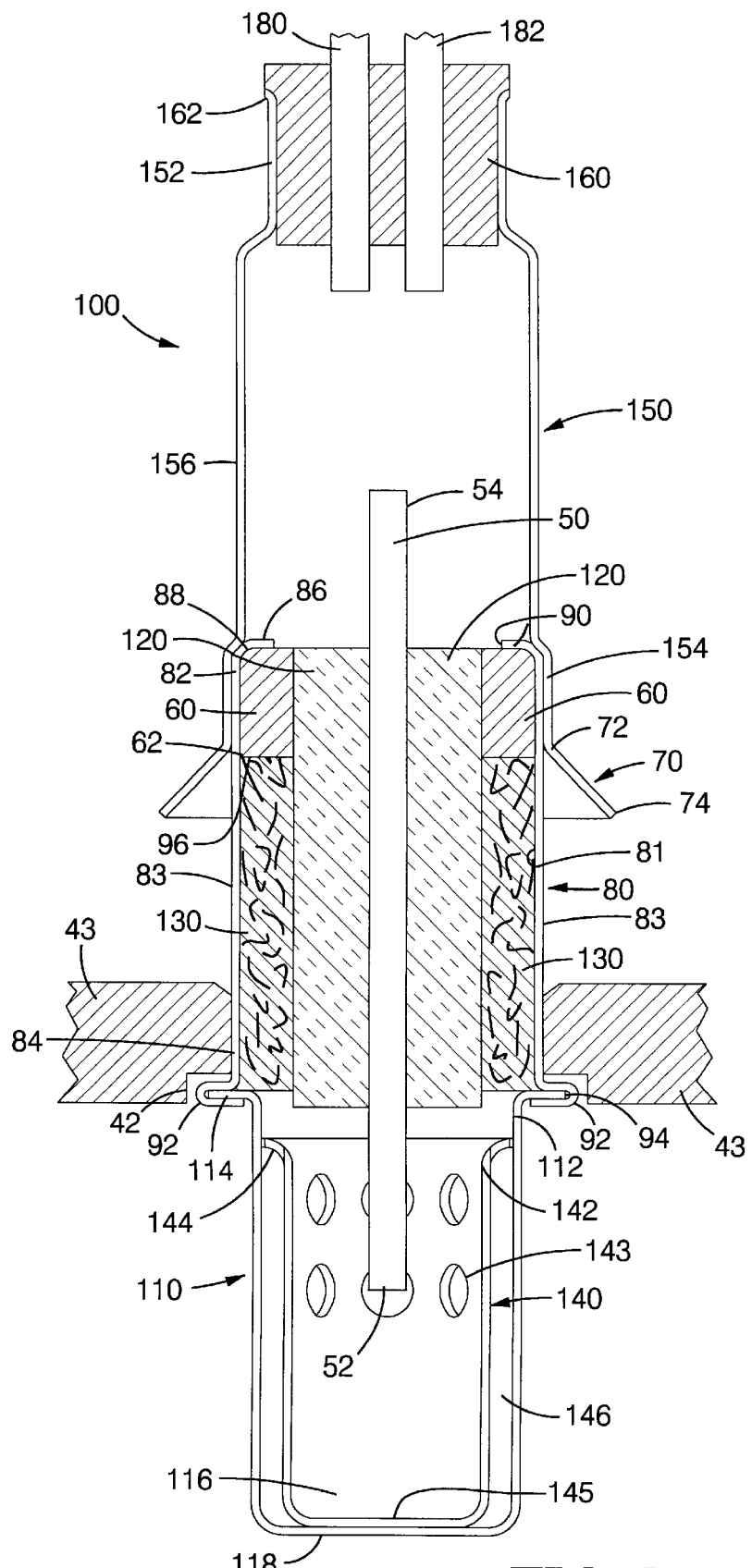
FIG. 2 is a cross-sectional side view of an exemplary embodiment of the exhaust constituent sensor of the present invention.
Figure 4:
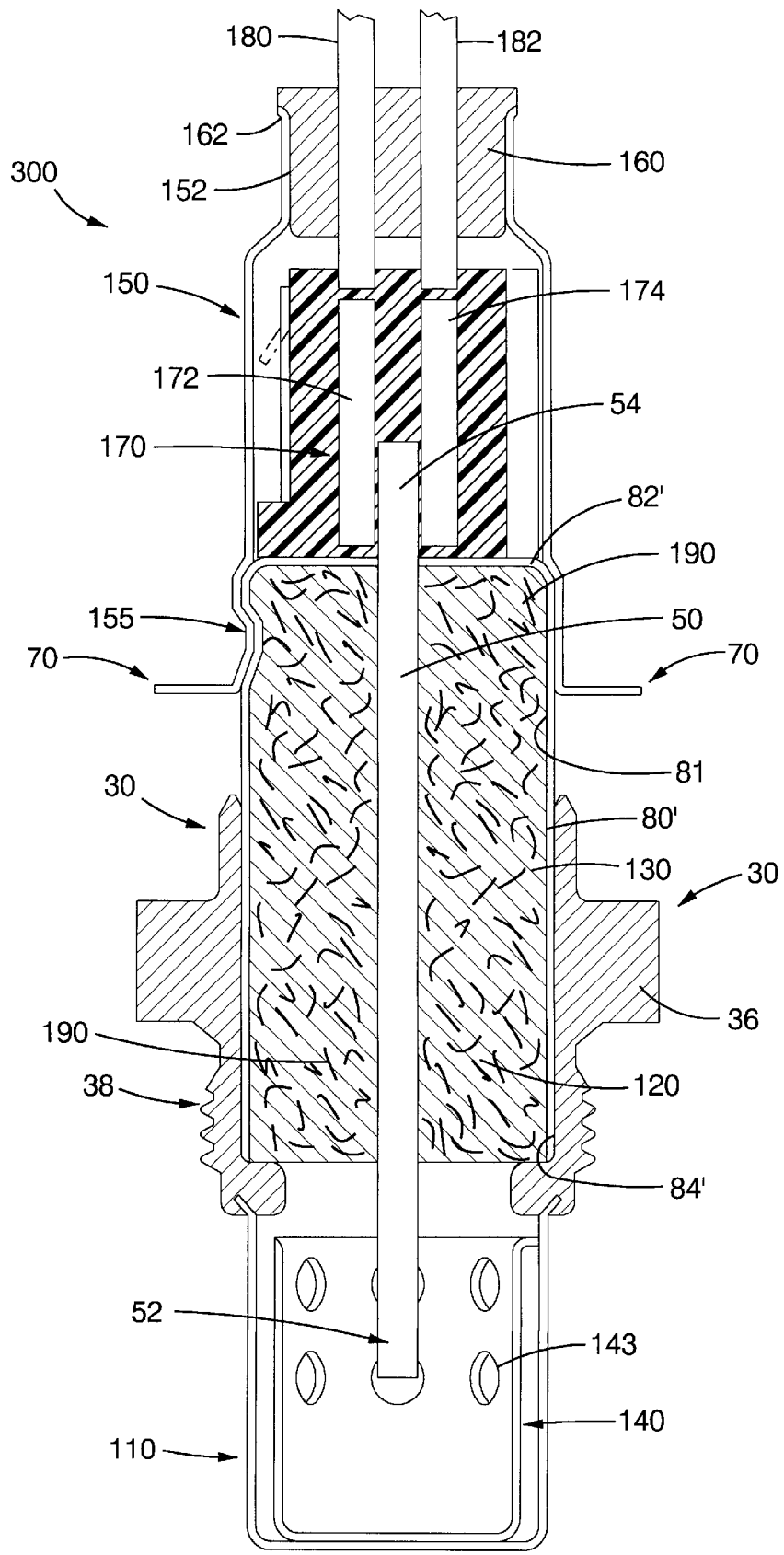
FIG. 4 is a cross-sectional side view of another exemplary embodiment of the exhaust constituent sensor of the present invention.

In accordance with the present invention, an annular heat fin or skirt 70 is optionally connected to outer surface 24 of tubular shield 20 with a predetermined angle α being formed between outer surface 24 and annular heat fin 70. The angle α at which annular heat fin 70 is disposed is not crucial to the present invention and it is within the scope of the invention that annular heat fin 70 may be disposed at any angle downward, as shown in FIG. 1 or, as shown in FIG. 4, substantially parallel to the exhaust pipe (not shown), or even angled upward, i.e. a greater than 90° (not shown). Annular heat fin 70 includes a first end 72 and a second end 74 which extends outwardly away from thermally conductive material 60 and planar sensing element 50. First end 72 may be integrally connected to outer surface 24 of upper shield 20 by known methods, including welding, or in the alternative, first end 72 may form a lower portion of an upper shield 150 when upper shield 150 engages and is secured to an intermediate shield 80, as is shown in FIG. 2. Annular heat fin 70 is designed to facilitate heat dissipation via thermal convection by providing an outer surface 76 which increases the general surface area available for thermal convection to occur and consequently results in the heat being dissipated more effectively and in a quicker manner than conventional exhaust constituent sensors. Preferably, annular heat fin 70 and more specifically first end 72 thereof is disposed at first end 62 of thermally conductive material 60 where the heat build up within exhaust constituent sensor 10 is typically higher than second end 64. This allows for even greater heat dissipation from inner cavity 56 of exhaust constituent sensor 10 by permitting for a greater convection surface on outer surface 76 of annular heat fin 70. Annular heat fin 70 may take a variety of shapes and forms to increase the area of outer surface 76, including ones that are sinuous in nature.

Advantageously, by transferring and dissipating heat in the above manner, the possibility that the electrical connection of the planar sensing element 50 will be exposed to excessive heat during its operation is greatly reduced or eliminated and more specifically, excessive heat is prevented from contacting the cable seal and terminal connection (not shown in FIG. 1) during normal operation of exhaust constituent sensor 10 within exhaust pipe 40. This is true because excessive heat which travels upward in exhaust constituent sensor 10 in a direction generally away from exhaust pipe 40 is drawn outward to outer surface 24 and is dissipated so that temperatures at a top portion of exhaust constituent sensor 10, where the electrical connection is made, are less than the temperatures at the opposite end of sensor 10 and are within an acceptable range. It is also within the scope of the present invention that a plurality of annular heat fins 70 may be used to transfer the heat from inner cavity 56 and effectively dissipate heat into the surrounding environment. When a plurality of annular heat fins 70 are used, they are annularly disposed around outer surface 24 of upper shield 20 at a predetermined spacing from one another.

Now turning to FIG. 2, an exemplary embodiment of an exhaust constituent sensor of the present invention, generally designated as 100, is illustrated. Exhaust constituent sensor 100 includes a housing structure generally formed of an upper shield 150, an intermediate shield 80, a lower shield 110, and an inner shield 140. In this embodiment, tubular shield 20 of FIG. 1 comprises upper shield 150 and intermediate shield 80. An inner support member 120, an outer support member 130, a portion of planar sensing element 50 and thermally conductive material 60 are disposed within intermediate shield 80. Intermediate shield 80 is a generally annular member which includes an open first end 82 and an open second end 84. At first end 82, intermediate shield 80 has an inwardly flared lip 86 which forms an inner shoulder 88 for contacting and positioning thermally conductive material 60 within intermediate shield 80 at first end 82 thereof. A central opening 90 defined by inwardly flared lip 86 permits end 54 of planar sensing element 50 to extend therethrough and electrically connect with at least one electrical terminal (not shown in FIG. 2). At second end 84, intermediate shield 80 has a crimped portion 92 which forms an annular recess 94 which receives and secures lower shield 110 to intermediate shield 80 upon mechanically securing the two members together by methods known in the art, e.g., crimping methods. Crimped portion 92 of intermediate shield 80 is also designed to engage a similarly shaped shoulder 42 formed in a support flange 43 which is mounted to an exhaust pipe (not shown). Accordingly, crimped portion 92 serves to locate and position exhaust constituent sensor 100 within support flange 43.

Also disposed within intermediate shield 80 are inner support member 120 and outer support member 130. Inner support member 120 is concentrically disposed around planar sensing element 50 and is provided for securely positioning and protecting planar sensing element 50 within exhaust constituent sensor 100, wherein ends 52 and 54 extend beyond inner support member 120 when assembled. Inner support member 120 has a central opening for receiving planar sensing element 50 which extends therethrough when exhaust constituent sensor 100 is assembled. Example material for inner support member 120 is steatite, rigid alumina, ceramic or other high temperature material providing the desired support, strength and thermal and electrical insulating properties in a spark ignition engine environment.

Outer support member 130 is disposed between inner support member 120 and an inner surface 81 of intermediate shield 80, wherein outer support member 130 extends from first end 62 of thermally conductive material 60 to second end 84 of intermediate shield 80. First end 62 of thermally conductive material 60 abuts against a first end 96 of outer support member 130. Outer support member 130 is preferably formed of alumina fibers, silica fibers, ceramic fibers or the like and is intended to support planar sensing element 50 and act as a thermal barrier. Similar to inner support member 120, outer support member 130 has a central opening sized to receive both inner support member 120 and planar sensing element 50. Inner support member 120, outer support member 130 and thermally conductive material 60 are retained in a desired position and secured within intermediate shield 80 upon securely coupling lower shield 110 with intermediate shield 80 and intermediate shield 80 with upper shield 150. While both inner support member 120 and outer support member 130 act as thermal and gas barriers, an amount of heat does travel upward toward the electrical connection of exhaust constituent sensor 100. However, the design of the present invention provides thermal management of such heat within exhaust constituent sensor 100.

With respect to the volumetric ratio of thermally conductive material 60 to outer support member 130, the volumetric ratio will vary for each individual sensor 100, depending upon known parameters, such as the temperature of the operating environment and the overall length of sensor 100. As previously discussed, outer support member 130 acts as a thermal barrier to prevent excessive heat from traveling upward toward the electrical connection of sensor 100 and these desired insulating properties must be balanced with the desired thermal transfer characteristics provided by thermally conductive material 60. As the volumetric amount of outer support member 130 decreases, the effectiveness of this material as a thermal barrier is reduced and consequently, a greater volume of heat having higher temperatures travels upward toward the terminal connection of sensor 100. At the same time, while a corresponding increase in the amount of thermally conductive material 60 relative to the volumetric amount of outer support member 130 leads to an increase in the amount of heat which is transported to the surrounding environment, the overall efficiency of the thermal transport mechanism may not be optimum. Accordingly, the volumetric ratio of thermally conductive material 60 to outer support member 130 should be such that the performance characteristics of each are optimized and excessive heat within sensor 100 is effectively prevented from traveling toward the terminal connection by outer support member 130 acting as a thermal barrier, while thermally conductive material 60 acts to effectively dissipate heat which travels upward within sensor 100 prior to that heat reaching the terminal connection.

Likewise, the present invention may be expressed generally in terms of a ratio between the length of thermally conductive material 60 to the length of outer support member 130. For example, the ratio of the length of thermally conductive material 60 to the length of outer support member 130 is preferably in the range between about 1:3 to about 1:10, depending upon the precise operating environment for sensor 100 and the overall length of the sensor. This recited ratio, e.g., about 1:3 to about 1:10, also corresponds to a suitable volumetric ratio between thermally conductive material 60 and outer support member 130, in view of the illustrated geometries of each in FIG. 2.

In addition, sensor 100 of the present invention may also be expressed in terms of a ratio between the length of thermally conductive material 60 and the length of intermediate shield 80 in which thermally conductive material 60 is disposed. For example, intermediate shield 80 of FIG. 2 has a length of about 32 mm and the length of thermally conductive material 60 is about 5 mm in this exemplary embodiment. This corresponds to a ratio between the length of thermally conductive material 60 to the length of intermediate shield 80 of about 1:6. It is within the scope of this invention that the ratio between the length of thermally conductive material 60 to the length of intermediate shield 80 may be in the range between about 1:4 to about 1:10. In other words, the length of thermally conductive material 60 may vary between about 3 mm to about 8 mm for a 32 mm length intermediate shield 80, depending upon the operating environment.

Lower shield 110 has an open end 112 which includes an outwardly flared lip 114, wherein outwardly flared lip 114 is disposed within annular recess 94 upon securing outwardly flared lip 114 to second end 84 of intermediate shield 80 by methods known in the art, preferably by a crimping action. Outwardly flared lip 114 may be further secured within annular recess 94 by welding it in place after crimping.

Lower shield 110 defines a sensing chamber 116 in which end 52 of planar sensing element 50 is disposed to permit contact with and sensing of exhaust gas. Lower shield 110 has a closed end 118 opposite open end 112 which is disposed within exhaust pipe 40 so that exhaust gas fluidly communicates with and is received into sensing chamber 116. Disposed within lower shield 110 is inner shield 140 which has an open end 142 including an outwardly flared lip 144. Open end 142 is sized to receive first end 52 of planar sensing element 50 and inner shield 140 further includes a closed end 145 adjacent and parallel to closed end 118 of lower shield 110. Lower shield 110 and inner shield 140 form a plurality of vents 146 for allowing passage of exhaust gas in and out of sensing chamber 116 so that the gasses may be sensed by planar sensing element 50. A plurality of openings 143 permits exhaust gas to flow into exhaust constituent sensor 100 and more specifically, exhaust gas flows through vents 146 into sensing chamber 116. It being understood that the sensors illustrated in the other Figures include openings 143 to permit exhaust gas to flow into the sensors.

Upper shield 150 of exhaust constituent sensor 100 comprises an elongated, generally annular member having an open first end 152 and an opposing open second end 154 and a middle section 156 extending therebetween. Middle section 156 tapers slightly inward toward first end 152 and tapers slightly outward toward second end 154, whereby the diameter of upper shield 150 at first end 152 is less than the diameter of upper shield 150 at second end 154. In an exemplary embodiment illustrated in FIG. 2, second end 154 of upper shield 150 is outwardly flared to form annular heat fin 70. Annular heat fin 70 extends outwardly from an outer surface 83 of intermediate shield 80 when upper shield 150 is secured to intermediate shield 80 and annular heat fin 70 is preferably formed so that first end 72 of annular heat fin 70 is disposed proximate first end 62 of thermally conductive material 60. As previously discussed hereinbefore, by positioning annular heat fin 70 and more specifically first end 72 proximate to first end 62 of thermally conductive material 60, a greater level of heat dissipation (transfer) results due to first end 62 being generally of a higher temperature than second end 64 because of its location relative to exhaust pipe 40. Consequently, it is advantageous to position and locate the convection means, namely annular heat fin 70, at a location where higher temperatures are present so that excessive heat is transferred to outer surface 83 and dissipated before the excessive heat is permitted to contact the electrical connection at one end of the exhaust constituent sensor 100. Preferably, end 154 of upper shield 150 has an increased diameter than first end 82 of intermediate shield 80 so that it may receive first end 82, whereby upper shield 150 is preferably secured in a leak-proof manner to first end 82 of intermediate shield 80 by a secure friction fit or other securing means known in the art, e.g., compressive forces exerted during assembly.

Figure 3:
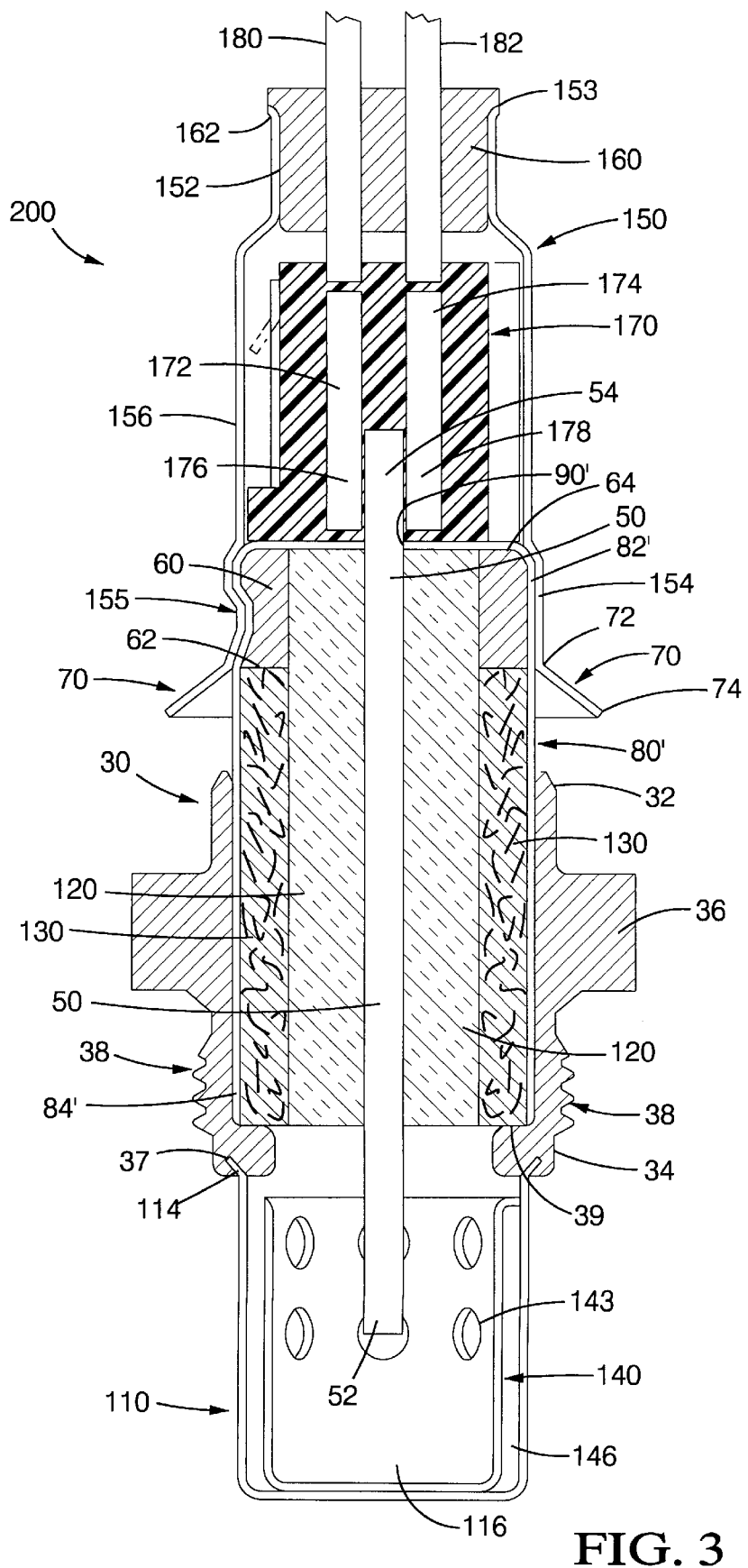
FIG. 3 is a cross-sectional side view of the exhaust constituent sensor of FIG. 2 further including a terminal connector disposed therein.

As shown in FIGS. 2 and 3, typically, a cable seal 160 is disposed within upper shield 150 at first open end 152, while a terminal connector 170 is disposed within upper shield 150 at middle section 156 when exhaust constituent sensor 100 is fully assembled, as shown in FIG. 3. Now turning to FIG. 3, which is a cross-sectional side view of another exemplary exhaust constituent sensor of the present invention, generally designated as 200. Exhaust constituent sensor 200 includes a housing structure formed of upper shield 150, intermediate shield 80', lower shield 110, inner shield 140 and shell 30. Exhaust constituent sensor 200 is generally similar to exhaust constituent sensor 100 with the exceptions that shell 30 is concentrically disposed around intermediate shield 80', intermediate shield 80' is slightly modified and lower shield 110 connects with shell 30 and not intermediate shield 80' as illustrated with reference to 80 and 110 in exhaust constituent sensor 100, as noted hereinafter in detail.

Intermediate shield 80' has a partially closed first end 82' and an open second end 84' opposite first end 82'. Instead of having the central opening 90 shown in FIG. 2, intermediate shield 80' has a centrally located annular opening 90' provided at first end 82' to receive end 54 of planar sensing element 50. Accordingly, both second end 64 of thermally conductive material 60 and one end of inner support member 120 abut and seat against partially closed first end 82'. Open second end 84' does not include crimped portion 92 and open second end 84 is disposed within an shoulder 39 formed in shell 30.

Shell 30 has a first end 32 and an opposite second end 34 and further includes a body portion 36 and a threaded portion 38 at second end 34. Body portion 36 is shaped to accommodate a wrench or other tool for tightening threaded portion 38 into a mount welded on exhaust pipe 40 or other component of an exhaust flow system enabling sensor chamber 116 to be located within a flow of exhaust gasses to be measured. First end 32 of shell 30 is disposed proximate second end 154 of upper shield 150 when shell 30 is concentrically disposed around intermediate shield 80' by means known in the art, with shell 30 preferably secured to intermediate shield 80' by being crimped thereto during the assembly process. Thus, shell 30 holds intermediate shield 80' and all components disposed within intermediate shield 80' in compressive force engagement.

Formed at second end 34 of shell 30 is inner shoulder 39 for contacting open second end 84' of intermediate shield 80' and securely positioning intermediate shield 80' with respect to shell 30. Also formed at second end 34 of shell 30 is an annular recess 37 for receiving outwardly flared lip 114 of the lower shield 110, wherein outwardly flared lip 114 is secured to second end 34 of shell 30 by disposing outwardly flared lip 114 into annular recess 37 and securing outwardly flared lip 114 therein by welding it in place or holding it in place by a secure friction fit.

The use of terminal connector 170 is known in the art and a suitable terminal connector 170 is also known in the art such as an edge card connector or a clam shell connector. Terminal connector 170 preferably includes a plurality of electrical terminals with each having a corresponding electrical wire connected thereto. For the purpose of illustration only, FIGS. 3 and 4 show an exhaust constituent sensor having a pair of electrical terminals 172 and 174, which are adapted to be connected to electrical wires 180 and 182, respectively, in a known manner. Electrical wires 180 and 182 pass through cable seal 160 which generally comprises a thermoplastic or a thermoset material suitable for use in a high temperature environment, such as an environment proximate the exhaust system of a motor vehicle. Cable seal 160, which is maintained in place by upper shield 150, is disposed at first end 152 of upper shield 150 whereby an upper end 153 of first end 152 forms a seat around a shoulder 162 of cable seal 160.

At end 54 of planar sensing element 50, lower ends 176 and 178 of terminals 172 and 174, respectively, contact external pads (not shown) on end 54 to provide electrical connection between terminals 172 and 174 and planar sensing element 50. Ends 176 and 178 of terminals 172 and 174, respectively, are maintained against end 54 of planar sensing element 50 by disposing end 54 between lower ends 176 and 178. Preferably, terminals 172 and 174 comprise spring terminals, the use of which is known in the art and the compressive force generated by disposing end 54 between spring terminals 172 and 174 securely maintains end 54 in electrical contact with spring terminals 172 and 174. However, it is within the scope of the present invention that a single terminal may be used and that other terminals besides spring terminals are suitable for use in the present invention.

Sensor 200 may be constructed according to methods known in the art, including, but not limited to, using crimping or other means to securely couple the outer components thereof. When crimping means are used, upper shield 150 is securely coupled to first end 82' of intermediate shield 80' so that end 54 of planar sensing element 50 is received within upper shield 150 and more particularly between terminals 172 and 174 to provide electrical connection between terminals 172 and 174 and planar sensing element 50. Upon crimping upper shield 150 to intermediate shield 80', a crimped portion 155 at second end 154 results. As disclosed hereinbefore, upper shield 150 optionally is provided with at least one annular heat fin 70 to provide the improved thermal transport mechanism according to the present invention and in an exemplary embodiment, annular heat fin 70 is located adjacent crimped portion 155. It being understood that when upper shield 150 is crimped to intermediate shield 80', crimped portion 155 will annularly extend around an outer surface of upper shield 150 and for the purpose of illustration only the cross-sectional views in the Figures shown an uncrimped portion opposite crimped portion 155. Meanwhile, lower shield 110 is securely coupled to shell 30 by engaging outwardly flared lip 144 of lower shield 110 with annular recess 37. Shell 30 is itself securely coupled to intermediate shield 80' by concentrically crimping shell 30 around intermediate shield 80'.

FIG. 4 is a cross-sectional view of an exhaust constituent sensor of another exemplary embodiment of the present invention, generally designated as 300. Exhaust constituent sensor 300 is very similar to sensor 200 with the notable exception that inner support member 120 has been eliminated and a fibrous material 190 is disposed between planar sensing element 50 and intermediate shield 80'. In this embodiment, fibrous material 190 extends from first end 82' to second end 84' of intermediate shield 80' and extends from inner surface 81 of intermediate shield 80' to planar sensing element 50 so that fibrous material 190 concentrically surrounds planar sensing element 50. In an exemplary embodiment, fibrous material 190 comprises a fibrous material formed of alumina fibers, silica fibers, ceramic fibers, or the like, including any mixture thereof. Generally, fibrous material 190 may be formed of any suitable fibrous material which is designed to be used in the high temperature environment of a spark ignition engine and provides the desired thermal management characteristics described hereinbefore.

For the structures shown in FIGS. 1–4, example material for the shields 20, 80, 80', 110, and 140 is high chrome or high nickel stainless steel, all steels chosen for high temperature endurance, high-strength and corrosion resistance. Terminal connector 170 may be a plastic or ceramic durable in the high temperature environments to which exhaust constituent sensors are exposed, while cable seal 160 is typically formed of a thermoplastic or thermoset material.

Thus in accordance with the present invention, an exhaust constituent sensor having improved thermal management is presented. Advantageously because of the improvement in thermal management of the sensor of the present invention, the overall length of the present sensor may be reduced without adversely effecting the operability of the sensor, especially the electrical connection of the sensor. This is of importance for a number of reasons, including that it represents a reduction in costs and it permits the sensor to be mounted in locations which were otherwise not accessible because of the previous more conventional length of the sensor. Alternatively, the length of the present sensor may be maintained at the longer conventional lengths; however, because of the improvement in thermal management, the sensor of the present invention may be used in an environment having greater temperatures. This provides greater versatility in positioning and mounting the sensor within the exhaust system. Finally, the sensor of the present invention also offers a simpler design and reduces manufacturing complexity and associated manufacturing costs by reducing time consuming steps in the manufacturing process.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An exhaust constituent sensor, comprising:

an elongated planar sensing element;

a tubular shield within which at least a portion of said planar sensing element extends;

a thermally conductive material disposed around at least a portion of said planar sensing element, said thermally conductive material disposed between said planar sensing element and said tubular shield, said thermally conductive material being in contact with said tubular shield; and a shell for mounting said tubular shield to a conduit through which exhaust flows.

2. The exhaust constituent sensor as set forth in claim 1 wherein said thermally conductive material is concentrically disposed around said planar sensing element.

3. The exhaust constituent sensor as set forth in claim 1 wherein said thermally conductive material is in contact with said planar sensing element.

4. The exhaust constituent sensor as set forth in claim 1 wherein said thermally conductive material comprises:
a high thermal conductivity metal mesh.

5. The exhaust constituent sensor as set forth in claim 1 further including:
at least one annular heat fin extending from an outer surface of said tubular shield for dissipating heat within said tubular shield via thermal convection.

6. The exhaust constituent sensor as set forth in claim 5 wherein said annular heat fin is disposed at a first end of said thermally conductive material, said first end of said thermally conductive material being located closer to said conduit than a second opposite end of said thermally conductive material.

7. The exhaust constituent sensor as set forth in claim 5 further including:
an upper shield secured to said tubular shield, said upper shield having a lower end which is outwardly flared away from said outer surface of tubular shield to form said annular heat fin.

8. The exhaust constituent sensor as set forth in claim 1 further including:
an inner support member disposed between said planar sensing element and said thermally conductive material, wherein said inner support member contacts both said thermally conductive material and said planar sensing element.

9. The exhaust constituent sensor as set forth in claim 8 wherein said inner support member is formed of steatite, a ceramic, or rigid alumina.

10. The exhaust constituent sensor as set forth in claim 1 wherein said tubular shield includes a first end and an opposite second end, said second end being located proximate said conduit and said first end extending away from said conduit; and wherein said thermally conductive material is disposed at said first end of said tubular shield.

11. The exhaust constituent sensor as set forth in claim 10 further including:
a terminal connection disposed at said first end of said tubular shield, said terminal connection providing an electrical connection between at least one electrical wire and said elongated planar sensing element, said thermally conductive material being disposed proximate said terminal connection to prevent excessive heat from contacting said terminal connection.

12. The exhaust constituent sensor as set forth in claim 10 further including:
at least one annular heat fin extending from an outer surface of said tubular shield for dissipating heat within said tubular shield via thermal convection;
an inner support member disposed between said planar sensing element and said thermally conductive material, said inner support member contacting both said thermally conductive material and said planar sensing element; and
an outer support member extending from said thermally conductive material to said second end of said tubular shield to act as a thermal barrier within said tubular shield.

13. The exhaust constituent sensor as set forth in claim 12 wherein said outer support member comprises:
alumina fibers, silica fibers, or ceramic fibers.

14. The exhaust constituent sensor as set forth in claim 12 wherein said outer support member is disposed between said inner support member and said tubular shield, said outer support member contacting both said inner support member and said tubular shield.

15. The exhaust constituent sensor as set forth in claim 12 wherein said outer support member has a length and said thermally conductive material has a length, and wherein a ratio of said length of said thermally conductive material to said length of said outer support member is in the range between about 1:3 to about 1:10.

16. The exhaust constituent sensor as set forth in claim 1 wherein said tubular shield has a length and said thermally conductive material has a length, and wherein a ratio of said length of said thermally conductive material to said length of said tubular shield is in the range between about 1:4 to about 1:10.

17. An exhaust constituent sensor, comprising:
an elongated planar sensing element;
a tubular shield within which at least a portion of said planar sensing element extends;
a fibrous material disposed around at least a portion of said planar sensing element, said fibrous material being in contact with both said planar sensing element and said tubular shield; and
a shell for mounting said tubular shield to a conduit through which exhaust flows.

18. The exhaust constituent sensor as set forth in claim 17 wherein said fibrous material comprises silica fibers, alumina fibers, or ceramic fibers.

19. The exhaust constituent sensor as set forth in claim 17 further including:
an annular heat fin or skirt extending from an outer surface of said tubular shield for dissipating heat within said tubular shield via thermal convection.

20. A method for thermal management of an exhaust constituent sensor, comprising:
providing an exhaust constituent sensor having a planar sensing element disposed within a tubular shield;
transferring heat within said tubular shield to an inner surface of said tubular shield by disposing a thermally conductive material between said planar sensing element and said tubular shield; and
dissipating said heat from an outer surface of said tubular shield into a surrounding environment.

21. The method as set forth in claim 20 further including:
disposing an annular heat fin on said outer surface of said tubular shield for dissipating said heat from said tubular shield via thermal convection.

22. The method as set forth in claim 20 wherein said thermally conductive material comprises:
a high thermal conductivity metal mesh.

23. The method as set forth in claim 20 wherein said thermally conductive material is disposed proximate a terminal connection at a first end of said tubular shield, said first end being located opposite a second end located proximate a conduit which carries a fluid to be sensed by said planar sensing element.

24. An exhaust constituent sensor, comprising:
an elongated planar sensing element;

a shield within which at least a portion of said planar sensing element extends;

a thermally conductive material disposed around at least a portion of said planar sensing element, said thermally conductive material disposed between said planar sensing element and said shield, said thermally conductive material being in contact with said shield; and a shell for mounting said shield to a conduit through which exhaust flows.

25. The exhaust constituent sensor of claim 24, wherein said thermally conductive material comprises a metal mesh.

26. The exhaust constituent sensor of claim 25, wherein said metal mesh has a mesh density of about 55% or less.

* * * * *